United States Patent [19]
Caretto et al.

[11] Patent Number: 6,057,295
[45] Date of Patent: *May 2, 2000

[54] OLIGOPEPTIDES DERIVED FROM C-REACTIVE PROTEIN FRAGMENTS

[75] Inventors: Patrizia Caretto; Flavio Leoni; Fabrizio Marcucci; Gianni Gromo; Paolo Mascagni; Massimo Pinori; Silvana Cappelletti, all of Sesto S. Giovanni, Italy

[73] Assignee: Italfarmaco S.p.A., Milan, Italy

[*] Notice: This patent is subject to a terminal disclaimer.

[21] Appl. No.: 08/624,405

[22] PCT Filed: May 16, 1994

[86] PCT No.: PCT/EP94/01574

§ 371 Date: Jun. 11, 1996

§ 102(e) Date: Jun. 11, 1996

[87] PCT Pub. No.: WO95/10531

PCT Pub. Date: Apr. 20, 1995

[30] Foreign Application Priority Data

Oct. 12, 1993 [IT] Italy .................. MI93A2154

[51] Int. Cl.$^7$ .................. A61K 38/00
[52] U.S. Cl. .................. 514/18; 530/330
[58] Field of Search .................. 530/330; 514/18

[56] References Cited

U.S. PATENT DOCUMENTS 4,353,823  10/1982  Chipens et al. .................. 260/112.5 R
5,521,159   5/1996  Verdini et al. .................. 514/18
5,578,575  11/1996  Verdini et al. .................. 514/18

FOREIGN PATENT DOCUMENTS 2945239  5/1981  Germany .

OTHER PUBLICATIONS

Hcaplus DN 112: 111693, Thiele et al., *Proc. Natl. Acad. Sci. USA*, 87 (1), 83–7, 1990.

Hcaplus DN 106: 61216, Hahn, WO 8604334, 1986.

Degrado, *Advances In Protein Chemistry*, vol. 39 pp. 51–118, 1988.

Buchta et al., Peptides (Fayetteville), 7(6), pp. 961–968, 1986.

Hocart et al., Innovation Perspect. Solid Phase Syn. Collect. Pap., Int. Symp., $1^{st}$ Meeting, 413–20, 1990.

Murphy et al., *Pept. Res.*, 1 (1), pp. 36–41, 1988.

Robey et al., *Journal of Biological Chemistry*, vol. 262, No. 15, pp. 7053–7057, 1987.

Fiedel, *Immunology*, 64, pp. 487–493, 1988.

Wieczorek et al., *Peptides*, vol. 15, No. 2, pp. 215–221, 1994.

*Primary Examiner*—Michael P. Woodward
*Assistant Examiner*—C. Delacroix-Muirheid
*Attorney, Agent, or Firm*—Walter H. Schneider

[57] ABSTRACT

Oligopeptides derived from fragments of C-reactive proteins and their use as immunomodulating agents in the therapy of cardiovascular and inflammatory diseases.

3 Claims, No Drawings

OLIGOPEPTIDES DERIVED FROM C-REACTIVE PROTEIN FRAGMENTS

The present invention relates to oligopeptides derived from fragments of the C-reactive protein (hereinafter CRP), and to their use as immuno-modulating agents, and in the therapy of cardiovascular and inflammatory diseases.

CRP is a protein generally having a very low blood concentration, which rises up to two thousand times following inflammatory processes [J. J. Morley and I. Kushner, Am. New York Acad. Sci., 389, 406–418 (1989)]. F. A. Robey et al., J. Biol. Chem., 262, No. 15, 7053–7057 (1987) disclose three CRP tetrapeptide sequences very similar to the ones of tuftsin. The chemically synthetized tetrapeptides stimulate the phagocytic leukocytes and the production of superoxide, and induce mononuclear cells to produce interleukin 1, in a tuftsin-like manner. Like tuftsin, the three CRP tetrapeptides are rapidly metabolized and inactivated by proteases in vivo.

It has been now surprisingly found that chemically modified analogues of said CRP tetrapeptide fragments are endowed with immuno-modulating activity and are useful in the therapy of cardiovascular and inflammatory diseases, for example in the therapy of the septic shock.

Therefore, the present invention relates to oligopeptides of formula (I)

$$A_1\text{-}A_2\text{-}A_3\text{-}A_4 \qquad (I)$$

wherein $A_1$ is an aminoacid residue selected from the group consisting of threonine, leucine, isoleucine, valine, sarcosine, alanine, glycine and $(C_{2-6})$acyl-glycine, or is absent;

$A_2$ is an aminoacid residue selected from the group consisting of leucine, isoleucine, valine, lysine, ornithine, Nα-substituted by at least one $(C_{1-6})$alkyl, benzyl or $(C_{2-6})$acyl group;

$A_3$ is an aminoacid residue selected from the group consisting of proline, leucine, isoleucine and valine;

$A_4$ is an aminoacid residue selected from the group consisting of arginine, leucine and glutamine, optionally amidated at the C-terminal position, or is an agmatine residue, or is absent;

with the proviso that only one of $A_1$, $A_2$ and $A_4$ may be absent; said compounds being further characterized in that the side-chain groups of the above aminoacid residues and of the agmatine residue may be optionally substituted by one or more groups selected from the group consisting of $(C_{1-6})$-alkyl, benzyl or $(C_{2-6})$acyl; and each of said aminoacid residues may be in D- or L-form at the Cα, or in form of one of the possible diastereoisomers or enantiomers;

and their salts with pharmaceutically acceptable acids or bases.

A preferred group of compounds according to the invention are the ones of formula (I) wherein $A_1$ is an aminoacid residue selected from the group consisting of glycine, threonine, leucine, isoleucine, valine, sarcosine, alanine $(C_{2-6})$acyl-glycine, or is absent; $A_2$ is an aminoacid residue selected from the group consisting of lysine Nα-substituted by a $(C_{1-6})$alkyl, benzyl or $(C_{2-6})$acyl group; $A_3$ is proline; $A_4$ is glutamine, leucine, arginine, optionally amidated at the C-terminal position, or an agmatine residue, or is absent; said compounds being further characterized in that the side-chain groups of said aminoacid residue and of the agmatine residue may be optionally substituted by one or more substituents selected from the group consisting of $(C_{1-6})$alkyl, benzyl or $(C_{2-6})$acyl; and each of said aminoacid residue may be in D or L form on the Cα, or in form of one of the possible diastereoisomers or enantiomers;

and the pharmaceutically acceptable acid or base salts thereof.

As $(C_{1-6})$alkyl it is intended a group such as methyl, ethyl, propyl, i-propyl, butyl, sec-butyl, tert.-butyl, n-pentyl, 3-methyl-pentyl, n-hexyl group, and the relevant positional isomers. As $(C_{2-6})$acyl it is intended a group such as formyl, acetyl, propionyl, butyryl, pentanoyl, hexanoyl and the relevant positional isomers.

Another object of the present invention relates to the use of the oligopeptides of formula (I) as immuno-modulating agents, and in the therapy of cardiovascular and inflammatory diseases, as the septic shock.

The compounds of the general formula (I) may be prepared employing peptide synthesis procedures, both in solid phase or in solution, known to the skilled in the art [see, for example, Merrifield, R. B., Biochemistry, 3, 1385 (1964)]. Unless otherwise mentioned, the aminoacid residues are intended to be used in L-configuration at the Cα.

Preferably, the synthesis is carried out in solution starting from the selected aminoacid and assembling the oligopeptide by a step-by-step addition of the desired aminoacids. Anyway, pre-constituted di- or tripeptide units may also be employed. Even if the synthesis of the oligopeptide may be started from any aminoacid, and may proceed both in the N-terminal or C-terminal direction, it is preferable to carried it out in the N-terminal direction. The aminoacids or, if desired, the pre-constituted di- or tripeptides may be used as such or in form of the relevant derivatives protected at the carboxy group by esterification, e.g. with tert.-butyl (tBu) group, or/and at the amine group by amidation, e.g. with benzyloxycarbonyl (Z), and, in case, suitably protected at the side-chain groups, e.g. with 2,2,5,7,8-pentametyl-chroman-6-sulfonyl (Pmc), tert.-butyloxycarbonyl (Boc) or trifluoroacetic acid (TFA). These protections may be effected by methods familiar to the skilled in the peptide chemistry.

Anyway, the above mentioned protected derivatives are commercially available products too. The protective group of the α-amino moiety is advantageously removed before the condensation with the subsequent aminoacid, for example through acidolysis with middle strong acids (e.g., trifluoroacetic acid), or through catalytic hydrogenolysis using gaseous hydrogen or hydrogen donors such as, for example, formic acid or salts thereof, triethylsylane, hydrazine in alkali, etc., selected in view of the aminoacid to deprotect and of the others, if present, in the presence of a suitable palladium catalyst. Then, the condensation with the subsequent aminoacid residue is carried out, such residue being suitably protected at the moieties not to be involved in said reaction.

Such condensation may be effected through one of the several known methods. Specifically, active esters may be used, e.g. succinimide (Su), fluoride (F), or condensing agents such as benzotriazol-1-yl-oxy-tris-(dimethylamino)-phosphonium hexafluorophosphate (BOP), bromo-tris-pirrolidium-phosphonium hexafluorophosphate (PyBroP), dicyclohexylcarbodiimide (DCC), etc., optionally in the presence of a catalyst such as 1-hydroxy-benzotriazole (HOBT), 4-dimethyl-amino-pyridine (DMAP), triethylamine (TEA), N-methyl-morpholine, N-methyl-imidazole etc.

As for the Nα-alkyl-derivatives of aminoacids, they are obtained by treatment with a suitable aldehyde, at low temperature, in the presence of acianoborohydride, selective reducing agent, in a polar solvent, preferably methanol.

When an oligopeptide of formula (I) having the C-terminal position in form of an amide is desired, commercially available aminoacids bearing such moiety may be employed as starting materials, or the C-terminal aminoacid may be amidated with an HOBT ammonium salt or, when $A_4$ is an agmatine residue, with agmatine itself.

The compounds of formula (I) wherein $A_1$ and/or $A_2$ are acylated aminoacid residues, are obtained by treatment with a suitable acyl-anhydride, at low temperature, in the presence of a catalyst such as DMAP. Alternatively, commercially available Nα-acyl-aminoacid residues may be employed.

The resulting products may be purified by crystallization from suitable solvents or, if necessary, by known chromatographic techniques such as reversed-phase chromatography and ion-exchange chromatography.

Hereinbelow, examples of preparation of some modified oligopeptides according to the invention are provided.

HPLC analysis of the aminoacid derivatives, of the protected fragments and of the modified oligopeptides were carried out at the following experimental conditions:
Column: Lichrosorb RP-18;
Temperature: 25° C. (unless otherwise mentioned)
Flow: 1.5 ml/min
Detector: Jasco 875-UV (230 nm)
Eluent A: 90% water, 10% acetonitrile, 0.1% trifluoroacetic acid (TFA)
Eluent B: acetonitrile, 0.1% TFA
Eluent C: water, 0.1% TFA
Gradients:

(I): from 0 to 40% B in A (20'), to 80% B in A (10')

(II): from 0 to 50% A in C (20'), to 100% A (3'), to 40% B in A 20'.

Unless otherwise mentioned, all the synthetic steps are carried out at room temperature.

The composition and the ratio of aminoacids were determined after hydrolysis with HCl 6M at 110° C. for 22 hours, by a Beckman SYSTEM GOLD aminoacid analyzer.

To be more clear, the meanings of the abbreviations employed in the following examples are listed hereinbelow:
BDHA-Cl—benzyldimethylhexadecylammonium chloride
Boc—tert.-butyloxycarbonyl
(Boc)20—di-tert.butyl-dicarbonate
BOP—benzotriazol-1-yl-oxy-tris-(dimethylammino)-phosphonium hexafluorophosphate
BSA—N,O-bis(trimethylsilyl)-acetamide
DCC—dicyclohexylcarbodiimide
DMAP—4-dimethylamino-pyridina
DMF—dimethylformamide
F—fluoride
HOBT—1-hydroxy-benzotriazole
Pmc—2,2,5,7,8-pentamethyl-chroman-6-sulfonyl
PyBrop—bromo-tris-pirrolidinium-phosphonium hexafluorophosphate
tBu—tert.-butyl
TBAF—tetrabutylammonium fluoride
TEA—triethylamine
TFA—trifluoroacetic acid
Su—succinimide
Z—benzyloxycarbonyl

EXAMPLE 1

H-Sar-Lys-Pro-Arg-OH.2AcOH

A] A slurry of 6.9 g (12 mmoles) of Z-Arg(Pmc)-OH in 60 ml of dichloroethane was added with 8.64 ml (36 mmoles) of N,N-dimethylformamide-di-tert.-butylacetale, in 60 minutes at 50° C. At the end of the addition, the reaction mixture was kept under stirring for 40 minutes at 50° C., then it was added with 20 ml of an aqueous solution of 5% sodium hydrocarbonate. The dichloroethane was evaporated under vacuum and the aqueous phase was diluted with 100 ml of ethyl acetate. The organic phase was separated and washed with an aqueous solution of 5% sodium hydrocarbonate and with a saturated aqueous solution of sodium chloride till neutrality. The organic phase was then anhydrified and evaporated under vacuum, and the resulting crude was purified on a silica gel column (eluent: ethyl acetate/n-hexane 6:4). There were obtained 3.4 g of Z-Arg(Pmc)-OtBu (HPLC, gradient (I): R.t. 32 min.; purity 99%).

B] A solution of 3.385 g (5.36 mmoles) of the compound under A] in 80 ml of methanol was added with 1.416 g (21.44 mmoles) of ammonium formate in 3 ml of water, and Pd sponge (about 1 g). The reaction mixture was slowly stirred for about 2 hours at room temperature. After filtering the catalyst off, the solvent was evaporated under vacuum, and the residue taken up in ethyl acetate and washed with an aqueous solution of 5% sodium hydrocarbonate, then with water till neutrality. The organic phase was anhydrified and evaporated under vacuum yielding 2.88 g of H-Arg(Pmc)-OtBu.HCOOH (HPLC, gradient (I): R.t. 23.40 min.; purity 99.3%).

C] The compound under B] was dissolved in 30 ml of DMF/methylene chloride 1:1. Separately, 1.403 g (5.63 mmoles) of Z-Pro-OH were dissolved in 20 ml of DMF/methylene chloride 1:1, added with BOP (2.49 g, 5.63 mmoles), HOBT (0.76 g, 5.63 mmoles) and TEA (1.56 ml, 11.26 mmoles). The two solutions were admixed and the resulting reaction mixture was stirred for 1 hour. The solvent was then evaporated under vacuum and the residue taken up in ethyl acetate and washed with 5% sodium hydrocarbonate and water till neutrality. The organic phase was anhydrified and evaporated under vacuum, and the residue was triturated in ethyl ether, thus yielding 3.71 g of Z-Pro-Arg(Pmc)-OtBu (HPLC, gradient (I): R.t. 29.49 min.; purity 99.6%).

D] A solution of 3.709 g (5.08 mmoles) of the compound under C], in 50 ml of methanol, was added with 350 mg of Pd/C under nitrogen, and sequentially, very slowly, with 4 ml (24 mmoles) of triethylsylane. After about 2 hours, the reaction mixture was filtered and the solvent evaporated under vacuum thus yielding 3.01 g of H-Pro-Arg(Pmc)-OtBu (HPLC, gradient (I): R.t. 24.25 min.; purity 99.56w).

E] The compound under D] (2.375 g, 4 mmoles) was dissolved in 20 ml of DMF/methylene chloride 1:1 v/v. Z-Lys(Boc)-OH (1.826 g, 4.8 mmoles) was dissolved in 20 ml of the same mixture, then added with BOP (2.12 g, 4.8 mmoles), HOBT (0.648 g, 4.8 mmoles) and TEA (1.33 ml, 9.6 mmoles). The two solutions were admixed and such reaction mixture was left under stirring for 1 hour, then was treated as described under C]. The residue was triturated in ethyl ether, thus yielding 3.64 g of Z-Lys(Boc)-Pro-Arg(Pmc)-OtBu.

F] A solution of 3.64 g (3.8 mmoles) of the compound under E], in 70 ml of methanol, was added with 1.321 g (20 mmoles) of ammonium formate in 3 ml of water, and about 1 g of fresh Pd sponge. The procedure described under B] was then applied yielding 3.27 g of H-Lys(Boc)-Pro-Arg(Pmc)-OtBu.

G] Z-Sar-OH (0.196 g, 0.88 mmole) was dissolved in 4 ml of DMF/methylene chloride 1:1 v/v, and sequentially added with BOP (0.39 g, 0.88 mmole), HOBT (0.119 g, 0.88 mmole), TEA (0.24 ml, 1.76 mmoles) and the compound under F] (0.694 g, 0.8 mmole) dissolved in 4 ml of the same mixture. The solution was left under stirring for 1 hour. The solvent was then evaporated under vacuum and the residue taken up in ethyl acetate and washed with 5% sodium hydrocarbonate, 2.5% potassium hydrogen sulfate and water till neutrality. The organic phase was anhydrified and evaporated under vacuum and the residue triturated in ethyl ether yielding 0.746 g of Z-Sar-Lys(Boc)-Pro-Arg(Pmc)-OtBu.

H] The compound under G] (0.746 g, 0.726 mmole) was dissolved in 10 ml of 95% TFA in water. After 75 minutes the reaction mixture was diluted with water and evaporated under vacuum. The residue was taken up in water, washed with ethyl ether and freeze-dried. The resulting product was purified by reversed-phase displacement chromatography. The product was dissolved in 3 ml of an aqueous solution of TFA (0.1% v/v) and charged at a flow of 0.5 ml/min on a VYDAC C18 column (250×10 mm) previously equilibrated with water containing TFA (0.1% v/v). The column was then eluted with a 50 mM aqueous solution of BDHA-Cl containing TFA (0.1% v/v), at 0.5 ml/min. After about 1 hour of elution, 0.5 ml-fractions were collected until the displacer elution. The fractions were analyzed by HPLC and the ones containing the pure product were joined and freeze-dried. There was obtained 0.2 g of Z-Sar-Lys-Pro-Arg-OH (HPLC, gradient (I): R.t. 11.04 min.; purity >95%).

I] The compound under H] (0.2 g, 0.28 mmole) was dissolved in 85% formic acid (5 ml) and added with fresh Pd sponge. The reaction mixture was left under mild stirring for 100 minutes. After filtering the catalyst off, the reaction mixture was diluted with water and freeze-dried. The product was purified by ion-exchange chromatography on an S-Sepharose F/F column (16× 200 mm), eluting with a gradient of ammonium acetate at pH 5 from 0.015M to 0.15M in 300 minutes, at 3 ml/min. The collected fractions were analyzed by HPLC and the ones containing the pure product were joined and freeze-dried more times yielding 0.1 g of the title product.

HPLC: gradient (II) R.t. 7.30 min., purity >99%.

FAB-MS: m/z-471 amu [M+H]+.

$^1$H-NMR (200 MHz; DMSO): d (1H; NH-Lys) 8.06; d (1H; NH-Arg) 7.17; m (1H; Cα-Pro) 4.63; m (1H; Cα-Lys) 4.32÷4.24; q (1H; Cα-Arg) 3.79; m (1H; Cδ-Pro) 3.70; s (2H; Cα-Sar) 3.05; t (3H; Cα-Arg) 3.03; t (2H; Cε-Lys) 2.75; s (3H; CH$_3$-Sar) 2.24; m (4H; Cβ+γ-Pro) 1.99÷1.85; s (6H; CH$_3$COO$^-$) 1.81; m (10H; Cβ+γ-Arg; Cβ+γ+δ-Lys) 1.72÷1.29.

EXAMPLE 2

H-(D)Ala-Lys-Pro-Arg-OH.2AcOH

Starting from 0.122 g (0.55 mmole) of Z-(D)Ala-OH and 0.434 g (0.5 mmole) of the compound of Example 1, F], and proceeding substantially as described in Example 1, G–I], there was obtained 0.089 g of the title product.

HPLC: gradient (II) R.t. 9.59 min., purity >99%.

FAB-MS: m/z-471 amu [M+H]+.

$^1$H-NMR (200 MHz; DMSO): d (1H; NH-Lys) 8.12; d (1H; NH-Arg) 7.17; m (1H; Cα-Pro) 4.60; m (1H; Cα-Lys) 4.31÷4.25; q (1H; Cα-Arg) 3.78; m (2H; Cδ-Pro) 3.70; q (1H; Cα-Ala) 3.31; t (2H; Cδ-Arg) 3.03; t (2H; Cε-Lys) 2.74; m (14H; Cβ+γ-Arg; Cβ+γ-Pro; Cβ+γ+δ-Lys) 2.09÷1.28; s (6H; CH$_3$COO$^-$) 1.80; d (3H; CH$_3$-Ala) 1.12.

EXAMPLE 3

Ac-Gly-Lys-Pro-Arg-OH.AcOH

Starting from Ac-Gly-OH (0.09 g, 0.77 mmole) and the compound of Example 1, F] (0.607 g, 0.7 mmole), and following the procedure of in Example 1, G–H], there was obtained 0.116 g of the title product.

HPLC: gradient (II) R.t. 13.06 min., purity >99%.

FAB-MS: m/z-499 amu [M+H]+.

$^1$H-NMR (200 MHz; DMSO): d (1H; NH-Lys) 8.15; t (1H; NH-Gly) 8.11; d (1H; NH-Arg) 7.47; m (1H; Cα-Pro) 4.59÷4.48; m (1H; Cα-Lys) 4.33÷4.25; m (5H; Cα-Arg; Cα-Gly; Cδ-Pro) 3.84÷3.59; t (2H; Cδ-Arg) 3.01; t (2H; Cε-Lys) 2.70; m (14H; Cβ+γ-Arg; Cβ+γ-Pro; Cβ+γ+δ-Lys) 2.03÷1.28; s (3H; CH$_3$COO$^-$) 1.85; s (3H; CH$_3$—CO—NH) 1.72.

EXAMPLE 4

H-Gly-(Et)Lys-Pro-Arg-OH.2AcOH

A] The compound of Example 1,F] (0.96 g, 1.1 mmoles) was dissolved in 8 ml of methanol and added with 0.071 g (1.12 mmoles) of sodium cyanoborohydride. The reaction mixture was cooled to −15° C. and added with 0.062 ml (1.12 mmoles) of acetaldehyde. After 60 minutes the reaction mixture was evaporated under vacuum and the residue was taken up in water and added with HCl till pH 3. The precipitate was filtered and washed with HCl pH-3. There was obtained 0.825 g of a white solid formed at 70% by H-(Et)Lys(Boc)-Pro-Arg(Pmc)-OtBu and at 26% by the dialkylation by-product.

B] Z-Gly-OH (0.994 g, 4.75 mmoles) was dissolved in ml 3 of DMF/methylene chloride (4:6 v/v), and sequentially added with PyBrop (2.21 g, 4.75 mmoles), diisopropylethylamine (2.4 ml, 14.25 mmoles) and the solid obtained under A] dissolved in 6 ml of the same mixture. The reaction mixture was left under stirring for 80 minutes. The solvent was then evaporated under vacuum and the residue taken up in ethyl acetate and washed with 5% sodium hydrocarbonate, 2.5% potassium hydrogen sulfate and water till neutrality. The organic phase was anhydrified and evaporated under vacuum. There was obtained 0.95 g of a mixture containing 60% of Z-Gly-(Et)Lys(Boc)-Pro-Arg(Pmc)-OtBu.

C] Starting from 0.75 g of the compound under B] and proceeding as described in Example 1, H], there was obtained 0.125 g of Z-Gly-(Et)Lys-Pro-Arg-OH.

HPLC: gradient (I) R.t. 12 min; purity 94%.

D] The compound under C] was purified by ion-exchange chromatography on a CM-Sephadex C-25 column (16× 200 mm) by eluting at 3 ml/min with a gradient of ammonium acetate at pH-6 from 0.02M to 0.2M in 270 minutes. The fractions collected were analyzed by HPLC and the ones containing the pure product were joined and freeze-dried more times yielding 0.1 g of Z-Gly-(Et)Lys-Pro-Arg-OH.2AcOH (ITF 1931).

HPLC: gradient (I) R.t. 12 min; purity 97.5%.

FAB-MS: m/z-619 amu [M+H]+.

$^1$H-NMR (200 MHz; DMSO): t (1H; NH-Gly) 7.46; m (5H; CH-aryl) 7.37; d (1H; NH-Lys) 7.24; m (1H; Cα-Lys)

5.19; s (2H; Cα-Arg) 5.05; m (1H; Cα-Pro) 4.23; m (2H; Cα-Gly) 3.92; m (1H; Cα-Arg) 3.81; m (2H; Cδ-Pro) 3.58; m (2H; CH$_2$-Et) 3.46; m (2H; Cδ-Arg) 2.99; m (2H; Cε-Lys) 2.65; m (4H; Cβ- and Cγ-Pro) 2.03÷1.76; m (19H; Cβ- and Cγ-Lys and -Arg, and Cδ-Lys) 1.69÷1.19; s (6H, CH$_3$COO$^-$) 1.66; t (3H, CH$_3$-Et) 1.04.

E] The compound under D] was treated as described in Example 1, I]. There was obtained 0.089 g of the title product.

HPLC: column temperature: 60° C.; gradient (II) R.t. 7.39 min., purity >99%.

FAB-MS: m/z-485 amu [M+H]+.

$^1$H-NMR (200 MHz; DMSO): d (1H; Nα-Arg) 7.12; m (0.8H; Cα-Pro) 5.24; m (0.2H; Cα-Pro) 4.43; m (1H; Cα-Lys) 4.28÷4.16; m (1H; Cα-Arg) 3.81; m (1H; Cδ-Pro e CH$_2$—N) 3.70÷3.16; s (2H; Cα-Gly) 3.41; t (2H; Cδ-Arg) 3.03; t (2H; Cε-Lys) 2.75; m (4H; Cβ+γ-Pro) 2.12÷1.75; s (6H; CH$_3$COO$^-$) 1.79; m (10H; Cβ-Arg; Cβ+γ+δ-Lys) 1.70÷1.14; t (2.4H; C*H$_3$—CH$_2$) 0.98; t (0.6H; C*H$_3$—CH$_2$) 0.89.

EXAMPLE 5

Ac-Lys-Pro-Arg-OH.TFA

A] The compound of Example 1, F] (0.3 g, 0.34 mmole) was dissolved in 1 ml of methylene chloride. The solution was cooled to −20° C. and added with DMAP (0.048 g, 0.38 mmole) and acetic anhydride (0.035 ml, 0.38 mmole). After 30 minutes the solution was washed with an aqueous solution of 5% sodium hydrocarbonate and with a saturated solution of sodium chloride. The organic phase was anhydrified and evaporated under vacuum yielding 0.28 g of Ac-Lys(Boc)-Pro-Arg(Pmc)-OtBu.

B] The compound under A] (0.28 g, 0.324 mmole) was treated as described in Example 1, H]. There was obtained 0.085 g of the title product.

HPLC: gradient (II) R.t. 13.64 min.; purity >99%.

FAB-MS: m/z-442 amu [M+H]+.

$^1$H-NMR (200 MHz; DMSO): d (0.15H; NH-Lys) 8.45; d (0.85H; NH-Lys) 8.21; d (1H; NH-Arg) 8.09; m (1H; Cα-Pro) 4.55÷4.45; m (1H; Cα-Lys) 4.43÷4.33; m (1H; Cα-Arg) 4.21÷4.11; m (2H; Cδ-Pro) 3.77÷3.47; q (2H; Cδ-Arg) 3.13; m (2H; Cε-Lys) 2.78; m (14H; Cβ+γ-Arg; Cβ+γ-Pro; Cβ+γ+δ-Lys) 2.18÷1.28; s (6H; C*H3COO— and C*H3-CO—NH) 1.84.

EXAMPLE 6

H-Gly-(D)Lys-Pro-Arg-OH.2AcOH

A] Starting from 0.544 g (1.43 mmoles) of Z-(D)Lys(Boc)-OH and 0.772 g (1.3 mmoles) of the compound of Example 1, D], and proceeding as described in Example 1, G], there were obtained 1.2 g of Z-(D)Lys(Boc)-Pro-Arg(Pmc)-OtBu.

B] The compound under A] (1.2 g, 1.29 mmoles) was dissolved in 30 ml of methanol and the solution was added with 0.325 g (5.16 mmoles) of ammonium formate in 0.3 ml of water, and about 0.2 g of fresh Pd sponge. After 2 hours the catalyst was filtered off and the solvent evaporated under vacuum. The residue was taken up in 50 ml of ethyl acetate and washed with 5% sodium hydrocarbonate in water and with water till neutrality. The organic phase was anhydrified and evaporated under vacuum yielding 1.119 g of H-(D)Lys(Boc)-Pro-Arg(Pmc)-OtBu.HCOOH.

C] Starting from 0.229 g (1.43 mmoles) of Z-Gly-OH and 1.119 g (1.29 mmoles) of the compound under B], and following the procedure of Example 1, G–I], there was obtained 0.23 g of the title product.

HPLC: gradient (II) R.t. 9.53 min., purity >99%.

FAB-MS: m/z-457 amu [M+H]+.

$^1$H-NMR (200 MHz; DMSO): d (1H; NH-Lys) 8.12; d (0.6H; NH-Arg) 7.37; d (0.4H; NH-Arg) 7.27; m (0.6H; Cα-Pro) 4.80; m (0.4H; Cα-Pro) 4.61; m (1H; Cα-Lys) 4.34÷4.15; q (0.6H; Cα-Arg) 3.95; t (0.4H; Cα-Arg) 3.81; m (2H; Cδ-Pro) 3.58÷3.35; s (0.4H; Cα-Gly) 3.26; s (0.6H; Cα-Gly) 3.11; t (2H; Cδ-Arg) 3.05; m (2H; Cε-Lys) 2.71; m (14H; Cβ+γ-Arg; Cβ+γ-Pro; Cβ+γ+δ-Lys) 2.11÷1.13; s (6H; CH$_3$COO$^-$) 1.79.

EXAMPLE 7

H-Gly-Lys-Pro-Arg-NH$_2$.3AcOH

A] Z-Arg(Pmc)-OH (2.87 g, 5 mmoles) was dissolved in 15 ml of DMF, then added with 0.837 g (5.5 mmoles) of HOBT ammonium salt, and the reaction mixture was cooled to 0° C. After the addition of 1.135 g (5.5 mmoles) of DCC, the reaction mixture was brought to room temperature and kept under stirring for 300 minutes. After filtering dicyclohexylurea off, the solvent was evaporated under vacuum and the residue taken up in 25 ml of ethyl acetate and washed with an aqueous solution of 5% sodium hydrocarbonate, then with water till neutrality. The organic phase was anhydrified, the solvent evaporated under vacuum and the residue crystallized from ethyl ether/n-hexane. There were obtained 2.8 g of Z-Arg(Pmc)-NH$_2$ [HPLC (gradient from 20 to 60% of B in A for 20 minutes): R.t. 15.7 min.; purity 98%].

B] A solution of 1.045 g (1.82 mmoles) of the compound under A] in 50 ml of methanol was added with 150 mg of Pd/C, under nitrogen, and sequentially, very slowly, with 2 ml (12 mmoles) of triethylsylane. After 120 minutes, the reaction mixture was filtered and the solvent evaporated under vacuum thus yielding 0.8 g of H-Arg(Pmc)-NH$_2$ [HPLC (gradient from 20 to 60% of B in A for 20 minutes): R.t. 8.6 min.; purity 98.5%].

C] Starting from Z-Pro-OH (0.499 g, 2 mmoles) and the compound under B] (0.8 g, 1.82 mmoles), and proceeding substantially as described in Example 1, G], there were obtained 1.2 g of Z-Pro-Arg(Pmc)-NH$_2$. This compound was dissolved in 25 ml of methanol and added with 100 mg of 10% Pd/C followed by a very slow addition of 1.52 ml (9.1 mmoles) of triethylsilane. After 130 minutes the reaction mixture was filtered and the solvent evaporated under vacuum, thus yielding 0.955 g of H-Pro-Arg(Pmc)-NH$_2$.

D] Starting from 0.745 g (1.96 mmoles) of Z-Lys(Boc)-OH and 0.955 g (1.78 mmoles) of the compound under C], and proceeding as described under C], 1.19 g of H-Lys(Boc)-Pro-Arg(Pmc)-NH$_2$ were obtained.

E] Starting from 0.385 g (1.71 mmoles) of Z-Gly-OH and 1.19 g (1.55 mmoles) of the compound under D], and proceeding as described in Example 1, G–I], there was obtained a crude which was then purified by ion-exchange chromatography through a 16×200 mm CM-52 cellulose column, eluting at 2 ml/min, with a gradient of ammonium acetate at pH 7 from 0.025M to 0.30M in 240 minutes. The collected fractions were analyzed by HPLC and the pure ones were joined and freeze-dried more times yielding 0.283 g of the title product.

HPLC: gradient (II) R.t. 4.7 min.; purity—99.3%.

FAB-MS: m/z-456 amu [M+H].

¹H-NMR (200 MHz; DMSO): d (0.2H; Nα-Arg) 8.89; m (1.8H; Nα-Lys and Nα-Arg) 8.16÷8.03; s (0.2H; NH$_2$-Arg) 7.77; s (0.8H; NH$_2$-Arg) 7.76; s (0.8H; NH$_2$-Arg) 7.07; s (0.2H; NH$_2$-Arg) 7.00; m (1H; Cα-Pro) 4.61÷4.50; m (1H; Cα-Lys) 4.47÷4.34; m (1H; Cα-Arg) 4.26÷4.15; m (2H; Cδ-Pro) 3.77÷3.54; s (2H; Cα-Gly) 3.13; m (2H; Cδ-Arg) 3.06; t (2H; Cε-Lys) 2.67; m (14H; Cβ+γ-Arg; Cβ+γ-Pro; Cβ+γ+δ-Lys) 2.12÷1.26; s (9H; CH$_3$COO⁻) 1.77.

EXAMPLE 8

H-Gly-Lys-Pro-Agm:3AcOH

A] Z-Lys-OH (0.84 g, 3 mmoles) was dissolved in 6 ml of a solution consisting of 3 ml of 1M sodium hydroxide and 3 ml of dioxane, and was then added with 0.57 ml (4.5 mmoles) of ethyl-thiol-trifluoroacetate. The reaction mixture was kept under stirring at 40° C. for about 7 hours, then the solvent was evaporated under vacuum and the residue taken up in 40 ml of 5% sodium hydrocarbonate. The aqueous phase was washed with ethyl acetate, brought to pH 2 and extracted with ethyl acetate. The organic phase was anhydrified and evaporated under vacuum, thus yielding 1 g of Z-Lys(TFA)-OH as an oil (HPLC, gradient (I): R.t. 19.7 min.; purity 96%).

B] H-Pro-OtBu.HCl (0.283 g, 1.364 mmoles) was dissolved in 9 ml of DMF/methylene chloride 1:1. The compound under A] (0.565 g, 1.5 mmoles) was dissolved in 9 ml of the same mixture, then was added with BOP (0.66 g, 1.5 mmoles), HOBT (0.202 g, 1.5 mmoles) and TEA (0.63 ml, 4.5 mmoles). The two solutions were joined and the resulting mixture was stirred for 30 minutes, then the procedure described in Example 1, G] was applied, thus obtaining 0.725 g of Z-Lys-(TFA)-Pro-OtBu as an oil (HPLC, gradient (I): R.t. 26.12 min.; purity 95.5%).

C] A solution of 0.725 g (1.36 mmoles) of the compound under B] in 20 ml of methanol was added with 80.26 g (4.1 mmoles) of ammonium formate dissolved in 0.1 ml of water, and about 0.2 g of fresh Pd sponge. After 2 hours the catalyst was filtered off and the solvent evaporated under vacuum. The residue was taken up in 40 ml of ethyl acetate and washed with 5% sodium hydrocarbonate in water, then with water till neutrality. The organic phase was anhydrified and evaporated under vacuum thus yielding 0.5 g of H-Lys(TFA)-Pro-OtBu.HCOOH (HPLC, gradient (I): R.t. 16.24 min.; purity 95%).

D] The compound under C] was dissolved in 10 ml of DMF/methylene chloride 1:1. Z-Gly-OH (0.291 g, 1.4 mmoles) was dissolved in 10 ml of the same mixture, then added with BOP (0.615 g, 1.4 mmoles), HOBT (0.188 g, 1.4 mmoles) and TEA (0.39 ml, 2.8 mmoles). The two solutions were joined and the resulting mixture was stirred for 60 minutes, then the procedure of Example 1, G] was substantially applied. The organic phase was anhydrified and evaporated under vacuum to yield an oily residue which was chromatographed on a silica gel column (eluent: ethyl acetate/n-hexane 9:1), thus yielding 0.588 g of Z-Gly-Lys(TFA)-Pro-OtBu (HPLC, gradient (I): R.t. 24.51 min.; purity 99.3%).

E] The compound under D] was dissolved in 15 ml of 37% HCl previously cooled to 0° C. After 8 minutes at 0° C., the reaction mixture was diluted with 15 ml of water and evaporated under vacuum. The residue was taken up in water, washed with ethyl ether and freeze-dried yielding 0.531 g of Z-Gly-Lys(TFA)-Pro-OH (HPLC, gradient (I): R.t. 17.69 min.; purity 95%).

F] The compound under E] (0.53 g, 1 mmole) was dissolved in 5 ml of ethyl acetate, added with 0.138 g (1.2 mmoles) of N-hydroxysuccinimide, and the reaction mixture was cooled to −20° C. There was then added 0.248 g (1.2 mmoles) of DCC. The reaction mixture was left at room temperature for 90 minutes, then the precipitate was filtered off and the solvent evaporated. There was obtained 0.625 g of Z-Gly-Lys (TFA)-Pro-OSu. Sodium hydrocarbonate (0.115 g, 1.09 mmoles) was dissolved in 22 ml of water and sequentially added with agmatine sulfate (0.498 g, 2.18 mmoles) and N-methyl-imidazole (0.087 ml, 1.09 mmoles). This solution was added with 0.57 g (0.91 mmole) of Z-GLy-Lys(TFA)-Pro-OSu. The reaction mixture was kept under stirring for 30 minutes at room temperature, then the mixture was brought to pH 3 and washed with ethyl acetate. The aqueous phase was freeze-dried. There was obtained 0.58 g of Z-Gly-Lys (TFA)-Pro-Agm.

G] The compound under F] was dissolved in 35 ml of water, and added with 1M sodium hydroxide till pH 12.7. After 30 minutes, the pH was brought to 7 by 1M HCl and the aqueous phase was freeze-dried. The resulting residue was taken up in absolute ethanol, the salts were filtered off and the solution was evaporated under vacuum. The product obtained was purified by reversed-phase displacement chromatography according to the procedure described in Example 1, H]. There was obtained 0.251 g of Z-Gly-Lys-Pro-Agm (HPLC, gradient (I): R.t. 10.77 min., purity 97.5%).

H] The compound under G] was treated substantially as described in Example 1, I]. There was obtained 0.229 g of the title compound.

HPLC: gradient (II) R.t. 10.93 min.; purity: 98.5%.

FAB-MS: m/z-413 amu [M+H]+.

¹H-NMR (200 MHz; DMSO): t (0.2H; Nα-Agm) 8.54; d (1H; Nα-Lys) 8.10; t (0.8H; Nα-Agm) 7.96; q (0.8H; Cα-Pro) 4.55; q (0.2H; Cα-Pro) 4.41; m (1H; Cα-Lys) 4.28÷4.22; m (2H; Cδ-Pro) 3.75÷3.34; m (6H; Cα-Gly; Cα+δ-Agm) 3.21÷2.93; t (2H; Cε-Lys) 2.67; m (14H; Cβ+γ-Agm; Cβ+γ-Pro; Cβ+γ+δ-Lys) 2.11÷1.25; s (9H; CH$_3$COO⁻) 1.76.

EXAMPLE 9

H-Gly-Lys-Pro-OH:AcOH

A] Z-Lys(Boc)-OH (1.487 g, 3.8 mmoles) was dissolved in 15 ml of DMF/methylene chloride (1:1 v/v) and added with, sequentially, BOP (1.72 g, 3.8 mmoles), HOBT (0.52 g, 3.8 mmoles), TEA (1.08 ml, 7.8 mmoles) and H-Pro-OtBu (0.623 g, 3 mmoles) dissolved in 15 ml of the same mixture. The solution was left under stirring for 1 hour. The solvent was then evaporated under vacuum, and the residue taken up in ethyl acetate and washed with 5% sodium hydrocarbonate in water, 2.5% potassium hydrogen sulfate in water, and water till neutrality. The organic phase was anhydrified and evaporated under vacuum, and the residue triturated in ethyl ether yielding 1.6 g of Z-Lys (Boc)-Pro-OtBu.

B] The compound under A] (1.59 g, 2.9 mmoles) was dissolved in 20 ml of methanol, and the resulting solution was added with ammonium formate (0.731 g, 11.6 mmoles) dissolved in 0.6 ml of water, and fresh Pd sponge (about 0.5 g). After 2 hours the catalyst was filtered off and the solvent was evaporated under vacuum. The residue was taken up in 50 ml of ethyl acetate and washed with 5% sodium hydrocarbonate in water and water till neutrality. The organic phase was anhydrified and evaporated under vacuum to yield 1.119 g of H-Lys(Boc)-Pro-OtBu.HCOOH.

C] Z-Gly-OH (0.762 g, 3.64 mmoles) was dissolved in 15 ml of DMF/methylene chloride (1:1 v/v) and sequentially added with BOP (1.61 go 3.64 mmoles), HOBT (0.491 g, 3.64 mmoles), TEA (1.01 ml, 7.28 mmoles) and H-Lys(Boc)-Pro-OtBu (1.119 g, 2.8 mmoles) dissolved in 15 ml of the same mixture. The reaction mixture was treated as described under A]. There were obtained 1.16 g of Z-Gly-Lys(Boc)-Pro-OtBu.

D] The compound under C] (0.746 g, 0.726 mmole) was dissolved in 20 ml of 95% TFA in water. After 1 hour the reaction mixture was diluted with water and evaporated under vacuum. The residue was taken up in water, washed with ethyl ether and freeze-dried. The resulting product was purified by displacement reversed-phase chromatography. The product was dissolved in 3 ml of an aqueous solution containing TFA (0.1% v/v) and charged on a VYDAC C18 column (250×10 mm) previously equilibrated with water containing TFA (0.1% v/v), at a flow of 0.5 ml/min. The column was then eluted at 0.5 ml/min, with a 50 mM aqueous solution of BDHA-Cl containing TFA (0.1% v/v). After about 1 hour of elution, 0.5 ml-fractions were collected until the elution of the displacer. The fractions were analyzed by HPLC, and the ones containing the pure product were joined and freeze-dried. There was obtained 0.325 g of Z-Gly-Lys-Pro-OH.

HPLC: gradient (I) R.t. 11.48 min.; purity HPLC >95%.

E] The compound under D] (0.325 g, 0.59 mmole) was dissolved in 5 ml of 85% formic acid and was added with fresh Pd sponge. The reaction mixture was left under mild stirring for about 1 hour. After filtering the catalyst off, formic acid was diluted with water and freeze-dried. The product was purified by means of ion-exchange chromatography on an S-Sepharose F/F column (16×200 mm) eluting at 3 ml/min with a gradient of ammonium acetate at pH 5 from 0.015M to 0.15M in 5 hours. The collected fractions were analyzed in HPLC and the ones containing the pure product were joined and freeze-dried more times to yield 0.165 g of the title product.

HPLC: gradient(II) R.t. 3.97 min.; purity: >99%.

FAB-MS: m/z-301 amu [M+H]+.

$^1$H-NMR (200 MHz; DMSO): d (1H; Nα-Lys) 8.17; m (1H; Cα-Pro) 4.60; m (1H; Cα-Lys) 4.14; m (2H; Cδ-Pro) 3.61; s (2H; Cα-Gly) 3.12; t (2H; Cε-Lys) 2.73; m (10H; Cβ+γ+δ-Lys; Cβ+γ-Pro) 2.62÷1.40; s (3H; $CH_3COO^-$) 1.88.

EXAMPLE 10

H-(Et)Lys-Pro-Arg-OH:2AcOH

A] 0.4 g of the compound of Example 4, A] was purified by silica gel chromatography on a Lobar LiChroprep Si 60 column, 40–63 μm (31×2.5 cm) previously equilibrated with chloroform/methanol (9/1 v/v). The column was then eluted with the same mixture at a flow of 8 ml/min. The fractions containing the pure product were joined and the solvent was evaporated under vacuum. There was obtained 0.28 g of H-(Et)Lys(Boc)-Pro-Arg (Pmc)-OtBu.

HPLC: gradient (I) R.t. 28.5 min.; purity >99%.

B] The compound under A] (0.28 g, 0.33 mmole) was dissolved in 6 ml of 95% TFA in water. After 70 minutes, the reaction mixture was diluted with water and evaporated under vacuum. The residue was taken up in water, washed with ethyl ether and freeze-dried. The product was purified by ion-exchange chromatography with a CM-Sephadex C-25 column (16×200 mm) by eluting at 3 ml/min with a gradient of ammonium acetate at pH-6 from 0.02M to 0.2M in 270 minutes. The collected fractions were analyzed by HPLC, and the ones containing the pure product were joined and freeze-dried more times, yielding 0.14 g of the title product.

HPLC: (column temperature: 60° C.) gradient (II) R.t. 7.15 min; purity >99%.

FAB-MS: m/z-$^{428}$ amu [M+H]+.

$^1$H-NMR (200 MHz; DMSO): d (1H; NH-Arg) 7.15; m (1H; Cα-Pro) 4.30; q (1H; Cα-Arg) 3.79; m (2H; Cδ-Pro) 3.64; m (1H; Cα-Lys) 3.41; m (2H; Cδ-Arg) 3.02; m (2H; Cε-Lys) 2.75; q (2H; $CH_2$-Et) 2.44; m (14H; Cβ- and Cγ-Pro, Lys and -Arg, Cδ-Lys) 2.11÷1.21; s (6H; $CH_3COO^-$) 1.80; t (3H; $CH_3$-Et) 0.97.

EXAMPLE 11

(Et)2Lys-Pro-Arg-OH.2AcOH

A] 0.425 g of the compound of Example 4, A] was dissolved in 7 ml of methanol and added with 0.063 g (1 mmole) of sodium cianoborohydride. The reaction mixture was cooled to −15° C. and added with 0.155 ml (2.5 mmoles) of acetaldehyde. After 90 minutes the reaction mixture was evaporated under vacuum and the residue slurried in water and added with HCl to pH-3. The resulting precipitate was filtered and washed with hydrochloric acid at pH-3. There were obtained 0.4 g of (Et)2Lys(Boc)-Pro-Arg(Pmc)-OtBu.

HPLC: gradient (I) R.t. 30.3 min.; purity >98%.

B] The compound under A] (0.4 g, 0.455 mmole) was treated as in Example 10, B]. There was obtained 0.14 g of the title product.

HPLC: (column temperature: 60° C.) gradient (II) R.t. 11.08 min.; purity >99%.

FAB-MS: m/z-456 amu [M+H]+.

$^1$H-NMR (200 MHz, DMSO): d (1H; NH-Arg) 7.08; m (1H; Cα-Pro) 4.21; m (3H; Cα-Arg and Cδ-Pro) 3.98÷3.65; m (1H; Cα-Lys) 3.54; m (2H; Cδ-Arg) 3.03; m (2H; Cε-Lys) 2.75; (2H; $CH_2$-Et) 2.38; m (2H; $CH_2$-Et) 2.36; m (4H; Cβ- and Cγ-Pro) 2.18÷1.81; s (6H; $CH_3COO^-$) 1.76; m (10H; Cβ- and Cγ-Lys and -Arg and Cδ-Lys) 1.74÷1.33; t (6H; $CH_3$-Et) 0.96.

EXAMPLE 12

H-Gly-(Et)Lys-Pro-Leu-OH.AcOH

A] The compound of Example 9, A] (5.33 g, 10 mmoles) was dissolved in 130 ml of absolute ethanol, in the presence of Pd/C. Acetaldehyde (0.745 ml, 12 mmoles) was then dropped in 30 minutes, dissolved in 20 ml of absolute ethanol, followed by triethylsilane (9.56 ml, 60 mmoles) in 60 minutes. After 75 minutes the catalyst was filtered off and the solvent evaporated under vacuum. The oily residue was dissolved in 50 ml of anhydrous ethyl ether and added with 3 ml of ethyl acetate saturated with HCl. The resulting precipitate was filtered and dried under vacuum. There were obtained 4.25 g of H-(Et)Lys(Boc)-Pro-OtBu.HCl.

HPLC: gradient (I) R.t. 19.83 min; purity >98%.

B] Z-Gly-OH (3.78 g, 18 mmoles) was dissolved in a mixture of 12 ml of DMF and 67 ml of methylene chloride. The solution was cooled to −15° C. and added with DCC (1.86 g, 9.03 mmoles). After 15 minutes the reaction mixture was filtered and added to the compound under A] (2.8 g, 6.02 mmoles) dissolved in 40 ml of methylene chloride. After the addition of N-methylmorpholine (0.66 ml, 6.02 mmoles) the reaction mixture was kept at 35° C. for 60 minutes. The solvent was evaporated under vacuum and the residue taken up in ethyl acetate and washed with 5% sodium hydrocarbonate in water and 2.5% potassium hydrogen sulfate in water. The organic phase was anhydrified and evaporated under vacuum. There were obtained 3.7 g of Z-Gly-(Et)Lys(Boc)-Pro-OtBu.

HPLC: gradient (I) R.t. 28.60 min; purity: 94%.

C] The compound under B] (3.7 g, 6 mmoles) was dissolved in 15 ml of 95% TFA in water. After 15 minutes the reaction mixture was slowly poured into ethyl ether and the resulting precipitate was filtered and dried under vacuum. There were obtained 2.9 g of Z-Gly-(Et)Lys-Pro-OH.

HPLC: gradient (I) R.t. 14.93 min; purity: 94%.

D] The compound under C] (1 g, 1.73 mmoles) was dissolved in 6.92 ml of dioxane/sodium hydroxide 0.5M in water (1/1 v/v). The solution was cooled to 0° C. and added with (Boc)20 (0.415 g, 1.903 mmoles). The reaction mixture was kept at room temperature for 45 minutes at pH-12. The solvent was evaporated under vacuum and the residue taken up in water and washed with ethyl ether. The aqueous phase was acidified till pH-3 and extracted in 30 ml of ethyl acetate. The organic phase was anhydrified and evaporated under vacuum. There was obtained 0.96 g of Z-Gly-(Et)Lys(Boc)-Pro-OH.

HPLC: gradient (I) R.t. 23.04 min; purity 92%.

E] The compound under D] (0.281 g, 0.5 mmole) was dissolved in 4 ml of DMF/methylene chloride 1:1, and added with BOP (0.221 g, 0.5 mmole), HOBT (0.067 g, 0.5 mmole), TEA (0.219 ml, 1.57 mmoles) and H-Leu-OtBu.HCl (0.117 g, 0.525 mmole). The procedure of Example 1, C] was then applied. There was obtained 0.365 g of Z-Gly-(Et)Lys(Boc)-Pro-Leu-OtBu.

HPLC: gradient (I) R.t. 29.86 min; purity >99%.

F] Starting from the compound under E] (0.365 g, 0.5 mmole), and substantially proceeding as described in Example 1, H–I], there was obtained 0.155 g of the title product.

HPLC: gradient (I) R.t. 6.3 min; purity 98%.

FAB-MS: m/z-442 amu [M+H]+.

$^1$H-NMR (200 MHz; DMSO): d (1H; NH-Leu) 6.93; m (1H; Cα-Lys) 5.23; m (1H; Cα-Pro) 4.15; m (1H; Cα-Leu) 3.84; m (6H; Cα-Gly, Cδ-Pro and CH2-Et) 3.72÷3.03; m (2H; Cε-Lys) 2.75; m (4H; Cβ- and Cγ-Pro) 2.17÷1.77; s (3H; CH$_3$COO$^-$) 1.85; m (9H; Cβ- and Cγ-Lys and -Leu, Cδ-Lys) 1.68÷1.05; t (3H; CH$_3$-Et) 0.96; d (3H; CH$_3$-Leu) 0.88; d (3H; CH$_3$-Leu) 0.86.

EXAMPLE 13

H-Gly-(Et)Lys-Pro-Agm.3AcOH

A] Starting from the compound of Example 12, D], (0.425 g, 0.75 mmole), N-hydroxysuccinimide (0.103 g, 0.9 mmole), DCC (0.186 g, 0.9 mmole), and sequentially adding sodium carbonate (0.095 g, 0.9 mmole), agmatine sulfate (0.411 g, 1.8 mmoles) and N-methyl-imidazole (0.072 ml, 0.9 mmole), the procedure of Example 8, F] was substantially applied. There was obtained 0.5 g of Z-Gly(Et)Lys(Boc)-Pro-Agm.

HPLC: gradient (I) R.t. 20.6 min; purity 85%.

B] Starting from the compound under A] (0.5 g, 0.74 mmole) and proceeding as described in Example 1, H–I], there was obtained 0.169 g of the title product.

HPLC: column temperature: 60° C.; gradient (II) R.t. 13.87 min; purity >99%.

FAB-MS: m/z-441 amu [M+H]+.

$^1$H-NMR (200 MHz; DMSO): t (1H; NH-Agm) 7.98; m (1H; Cα-Lys) 5.26; m (1H; Cα-Pro) 4.15; m (10H; Cα-Gly, Cα-Agm, Cδ-Pro, Cδ-Agm and CH$_2$-Et) 3.65÷2.91; m (2H; Cε-Lys) 2.66; m (14H; Cβ- and Cγ-Lys, -Pro and -Agm, and Cδ-Lys) 2.18÷1.16; s (9H; CH$_3$COO$^-$) 1.76; t (3H; CH$_3$-Et) 0.99.

EXAMPLE 14

H-Gly-(Et)Lys-Pro-OH.2AcOH

Starting from the compound of Example 12, C] (0.2 g, 0.347 mmole) and proceeding as described in Example 1, I], there was obtained 0.085 g of the title product.

HPLC: (column temperature: 60° C.); gradient (II) R.t. 9.32 min; purity >99%.

FAB-MS: m/z-329 amu [M+H]+.

$^1$H-NMR (200 MHz; DMSO): m (1H; Cα-Lys) 5.16; m (1H; Cα-Pro) 4.05; m (6H; Cα-Gly and Cδ-Pro and CH$_2$-Et) 3.87÷2.92; m (2H; Cε-Lys) 2.67; m (4H; Cβ- and Cγ-Pro) 2.10÷1.65; s (6H; CH$_3$COO$^-$) 1.78; m (6H; Cβ+γ+δ-Lys) 1.59÷1.24; t (1.3H; CH$_3$-Et) 1.06; t (1.7H; CH$_3$-Et) 1.02.

EXAMPLE 15

H-Leu-(Et)Lys-Pro-Arg-OH.2AcOH

A] The compound of Example 12, A] (0.732 g, 1.5 mmoles) was dissolved, under nitrogen, in 8 ml of acetonitrile. There was then added 0.733 ml (3 mmoles) of BSA, 1.6 g (6 mmoles) of Z-Leu-F (L. A. Carpino, E. M. E. Mansour, D. Sadat-Aalaee, J. Org. Chem., 1991, 56, 2611–2614) and 0.094 g (0.3 mmole) of TBAF dissolved in 2 ml of acetonitrile. The reaction mixture was kept under stirring for 240 minutes at room temperature. The solvent was then evaporated under vacuum and the residue taken up in ethyl acetate and washed with 5% sodium hydrocarbonate and 2.5% potassium hydrogen sulfate till neutrality. The organic phase was anhydrified and evaporated under vacuum and the residue was purified by silica gel chromatography using a Lobar LiChroprep Si 60 column, 40–63 mm, (44×3.7 cm) previously equilibrated in hexane/ethyl acetate (7/3 v/v). The column was eluted with the same mixture at 16 ml/min. The fractions containing the pure product were collected and the solvent evaporated under vacuum. There was obtained 0.5 g of Z-Leu-(Et)Lys(Boc)-Pro-OtBu.

HPLC: gradient (I) R.t. 31.5 min; purity 94%.

B] The compound under A] (0.5 g, 0.74 mmole) was treated as described in Example 12, C–D]. There was obtained 0.43 g of Z-Leu-(Et)Lys(Boc)-Pro-OH.

HPLC: gradient (I) R.t. 31.5 min; purity >98%.

C] The compound under B] (0.43 g, 0.695 mmole) was dissolved in 9 ml of 1,2-dimethoxyethane and added with N-hydroxysuccinimide (0.128 g, 1.112 mmoles) and, after cooling to −20° C., DCC (0.215 g, 1.042 mmoles). After 15 minutes the reaction mixture was filtered and the resulting solution was added with H-Arg-OH dissolved in 21 ml of DMF/KCl 0.15M in water (2/1 v/v). The reaction mixture was kept under stirring for 110 minutes at room temperature. The solvent was then evaporated under vacuum and the residue taken up more times in absolute ethanol, and filtered. There was obtained 0.455 g of Z-Leu-(Et)Lys(Boc)-Pro-Arg-OH.

HPLC: gradient (I) R.t. 24.38 min; purity 84%.

D] The compound under C] was treated as described in Example 1, H], thus yielding Z-Leu-(Et)Lys-Pro-Arg-OH.TFA (ITF 1929).

HPLC: gradient (I) R.t. 17.63 min; purity 98%.

FAB-MS: m/z-676 amu [M+H]+.

$^1$H-NMR (200 MHz; DMSO): t (1H; NHε-Arg) 7.77; d (1H; NH-Leu) 7.68; m (5H; CH-aryl) 7.37; d (1H; NHα-

Arg) 7.34; m (1H; Cα-Lys) 5.15; s (2H; CH$_2$-Z) 5.03; m (1H; Cα-Leu) 4.42; m (1H; Cα-Pro) 4.26; m (1H; Cα-Arg) 3.99; m (4H; Cδ-Pro and CH$_2$-Et) 3.68÷3.18; m (2H; Cδ-Arg) 3.11; m (2H; CHε-Lys) 2.74; m (17H; Cβ and Cγ-Leu, -Lys, -Pro and -Arg, and Cδ-Lys) 2.18÷1.19; t (3H; CH$_3$-Et) 1.12; d (6H; CH$_3$-Leu) 0.89.

E] The compound under D] (0.341 g, 0.44 mmole) was treated as described in Example 1, I]. There was obtained 0.06 g of the title product.

HPLC: gradient (II) R.t. 29.13 min; purity 97%.

FAB-MS: m/z-541 amu [M+H]+.

$^1$H-NMR (200 MHz; DMSO): d (1H; NH-Arg) 7.10; m (1H; Cα-Lys) 5.20; m (1H; Cα-Pro) 4.19; m (1H; Cα-Arg) 3.81; m (5H; Cα-Lys, CH$_2$-Et and Cδ-Pro) 3.66÷3.10; m (2H; Cδ-Arg) 3.03; m (2H; Cε-Lys) 2.74; m (17H; Cβ and Cγ-Leu, -Lys, -Pro and -Arg, and Cδ-Lys) 2.10÷1.18; s (6H; CH$_3$COO$^-$) 1.77; t (3H; CH$_3$-Et) 1.03; d (3H; CH$_3$-Leu) 0.89; d (3H; CH$_3$-Leu) 0.87.

EXAMPLE 16

H-Gly-(isoBu)Lys-Pro-Arg-OH.2AcOH

A] The compound of Example 9, B] (2.38 g, 5.95 mmoles) was dissolved in 34 ml of methanol and added with 20.4 ml of acetic acid. The reaction mixture was cooled to −20°0 C. and, after dropping isobutyraldehyde (1.36 ml, 14.87 mmoles), added with sodium cianoborohydride (0.748 g, 11.9 mmoles). The reaction mixture was kept under stirring for 100 minutes at room temperature. The solvent was then evaporated under vacuum and the residue was taken up in ethyl acetate and washed with 5% sodium carbonate, HCl at pH-2.5 and water till neutrality. The organic phase was anhydrified and evaporated under vacuum. There were obtained 2.65 g of H-(isoBu)Lys(Boc)-Pro-OtBu.

HPLC: gradient (I) R.t. 22.85 min; purity 97%.

B] Starting from the compound under A] (2.2 g, 4.8 mmoles) and Z-Gly-F (4.2 g, 20 mmoles) and substantially operating as described in Example 15, A–D], there was obtained 0.2 g of the title product.

HPLC: gradient (II) R.t. 12.58 min; purity >98%.

FAB-MS: m/z-513 amu [M+H]+.

$^1$H-NMR (200 MHz; DMSO): d (1H; NH-Arg) 7.09; m (1H; Cα-Lys) 5.25; m (0.3H; Cα-Pro) 4.43; m (0.7H; Cα-Pro) 4.16; m (3H; Cα-Arg and Cδ-Pro) 3.83÷3.56; m (2H; Cα-Gly) 3.38; m (4H; CH$_2$-iBu and Cδ-Arg) 3.09÷2.93; m (2H; Cε-Lys) 2.75; m (15H; Cβ- and Cγ-Lys, -Pro and -Arg, Cδ-Lys and CH-iBu) 2.13÷1.16; s (6H; CH$_3$COO$^-$) 1.79; d (2.1H; CH$_3$-iBu) 0.81; d (3H; CH$_3$-iBu) 0.76; d (0,9H; CH$_3$-iBu) 0.69.

EXAMPLE 17

H-Gly-(isoBut)Lys-Pro-OH.AcOH

Starting from the compound obtained in Example 16, A] (0.455 g, 1 mmole) and Z-Gly fluoride (0.84 g, 4 mmoles), and substantially operating as described in Examples 15, A] and then 10, B], there was obtained 0.172 g of the title product.

HPLC: (column temperature: 60° C.), gradient (II) R.t. 23.48 min; purity >98%.

FAB-MS: m/z-357 amu [M+H]+.

$^1$H-NMR (200 MHz; DMSO): m (1H; Cα-Lys) 5.13; m (0.3H; Cα-Pro) 4.30; m (0.7H; Cα-Pro) 4.00; m (4H; Cα-Gly and Cδ-Pro) 3.68÷3.31; m (2H; CH$_2$-iBu) 3.03; m (2H; C-Lys) 2.81÷2.61; m (11H; Cβ and Cγ-Lys and -Pro, Cδ-Lys and CH-iBu) 2.05÷1.24; s (3H; CH$_3$COO$^-$) 1.86; d (2.1H; CH$_3$-iBu) 0.82; d (3H; CH$_3$-iBu) 0.77; d (0,9H; CH$_3$-iBu) 0.69.

EXAMPLE 18

H-Gly-(Bzl)Lys-Pro-Arg-OH.2AcOH

Starting from the compound of Example 9, B] (1.36 g, 3 mmoles) and benzaldehyde (0.546 ml, 5.4 mmoles), and substantially following the procedure of Example 16, A–B], there was obtained 0.395 g of the title product.

HPLC: gradient (II) R.t. 27.85 min; purity >99%.

FAB-MS: m/z-546 amu [M+H]+.

$^1$H-NMR (200 MHz; DMSO): m (6H; CH-aryl and NH-Arg) 7.39÷6.97; m (0.7H; Cα-Lys) 5.42; m (0.3H; Cα-Lys) 4.93; m (2H; Cα-Pro and Cα-Arg) 4.65÷4.42; m (4H; Cα-Gly and Cδ-Pro) 4.00÷3.43; m (2H; CH$_2$-aryl) 3.30; m (2H; Cδ-Arg) 3.03; m (2H; Cε-Lys) 2.75; m (14H; Cβ- and Cγ-Lys, -Pro and -Arg, and Cδ-Lys) 2.29÷1.14; s (6H; CH$_3$COO$^-$) 1.79.

EXAMPLE 19

H-Gly-Pro-Pro-Arg-OH.AcOH

A] Starting from H-Pro-OtBu.HCl (0.315 g, 1.5 mmoles) and Z-Pro-OH (0.397 g, 1.59 mmoles) the procedure of Example 1, C–D] was substantially applied. There was obtained 0.4 g of H-Pro-Pro-OtBu.

HPLC: gradient (I) R.t. 11.38 min; purity 93%.

B] Starting from Z-Gly-OH (0.333 g, 1.59 mmoles) and the compound under A] (0.4 g, 1.5 mmoles), the procedure of Example 1, G–H] was substantially applied, thus obtaining 0.6 g of Z-Gly-Pro-Pro-OH.

HPLC: gradient (I) R.t. 14.81 min; purity >98%.

C] The compound under B] was treated substantially as described in Example 15, C–D]. There was obtained 0.045 g of the title product.

HPLC: (column temperature: 60° C.) gradient (II) R.t. 12.06 min; purity >98%.

FAB-MS: m/z-426 amu [M+H]+.

$^1$H-NMR (200 MHz; DMSO): d (1H; NH-Arg) 7.34; m (0.2H; Cα-Pro) 4.73; m (0.8H; Cα-Pro) 4.61; m (0.2H; Cα-Pro) 4.39; m (0.8H; Cα-Pro) 4.33; m (7H; Cα-Arg and -Gly, and 2Cδ-Pro) 3.83÷3.26; m (2H; Cδ-Arg) 3.00; m (12H; Cβ- and Cγ-Pro and -Arg) 2.22÷1.26; s (3H; CH$_3$COO$^-$) 1.83.

The compounds of the present invention showed to be endowed with immunoregulating, cardiovascular and antinflammatory activity. In particular, they showed to be useful as therapeutic agents against septic shock. This activity was determined by means of the following pharmacological test.

BALB/c female mice, weighing 20–22 g, were intraperitoneally inoculated with 1 mg/mouse of LPS (lipopolysaccharide sierotype 0127:B8—Sigma) in 0.5 ml of physiological solution. Thereafter they were subdivided into groups 10 animals, each intraperitoneally inoculated with 62.5 μg/mouse of some of the compounds representative of the invention, 20 and 120 minutes after the administration of LPS. One group of animals was treated with LPS only and considered as the control.

The animals were monitored for at least 4 days. The results are set forth in the following Table.

TABLE

| Example | Survival percentage |
| --- | --- |
| (control) | 3.5 |
| 2 | 23 |
| 4 | 40 |
| 5 | 23 |

TABLE-continued

| Example | Survival percentage |
|---|---|
| 14 | 38 |
| 19 | 23 |

The cardiovascular activity of the compounds of the invention was investigated by means of a test aiming at evaluating the cardioprotective activity following ischemia induced by the occlusion of the left coronary artery in the anesthetized rat, performed substantially as described by C. Clark et al. Journ., Exp. Methods, 3, 357, 1980. It is known that the occlusion of the coronary artery caused a lot of events altering the ECG-pattern including, among others, hypoxia, arrhythmias, with eventual death of the laboratory animals.

In this test, male Charles River rats, subdivided into groups of 12 animals, were anesthetized with nembutal (65 mg/kg i.p.) and connected to an electrocardiograph for continuosly monitoring the ECG. Subsequently, the animals underwent thoracotomy and, after incision of the pericardium, a suture thread was passed around and the left coronary artery, close to its beginning. After a recovery of 10 minutes, and provided that no electrocardiographic alteration was recorded, the animals were administered i.v. with predetermined dosages of the compounds of the invention dissolved or suspended in saline. One group of animals (controls) were administered i.v. with saline. After 5 minutes the left coronary artery was ligated and the ligature was maintained for 30 minutes.

In representative experiments, a significant reduction of the ventricular tachycardia (VT), ventricular fibrillations (VF) and mortality was observed even at dosages of 0.4 $\mu$g/kg. In particular, it was found that the compound of Example 4, when administered at 3 $\mu$g/kg, caused a reduction of the mortality occurring in the first 18 minutes from the ligature of about 80% over the controls, whereas VT and VF were reduced of about 50%.

Object of the present invention is also the use of the new oligopeptide as immuno-modulating agents, and in the treatment of cardiovascular and inflammatory pathologies, referring to all the industrial aspects connected to said use also including the pharmaceutical compositions thereof. Examples of such pharmaceutical compositions are tablets, sugar coated and film coated tablets, syrups and phials, the latters being suitable both for the oral and the intramuscolar or endovenous administration. Such compositions contain the active principle alone or in combination with common pharmaceutically acceptable carriers and excipients.

The dosage of active principle may vary within wide ranges depending on the compound employed which may be administered one or more times a day according to the therapeutic needs.

We claim:

1. An oligopeptide having the following aminoacid residue sequence

Gly-(Et)Lys-Pro-Arg and the pharmaceutically acceptable acid or base salts thereof.

2. A pharmaceutical composition having anti-inflammatory activity comprising as the principal active ingredient an oligopeptide according to claim 1 in admixture with a pharmaceutically acceptable carrier.

3. A method of treating a patient suffering from an inflammatory disease which comprises administering to said patient an effective amount of a composition according to claim 2.

* * * * *

```
                        SEQUENCE LISTING (1) GENERAL INFORMATION:

(iii) NUMBER OF SEQUENCES: 11

(2) INFORMATION FOR SEQ ID NO: 1:

(i) SEQUENCE CHARACTERISTICS:
         (A) LENGTH: 4 amino acids
         (B) TYPE: amino acid
         (C) STRANDEDNESS:
         (D) TOPOLOGY: linear (ii) MOLECULE TYPE: peptide (iii) HYPOTHETICAL: NO (iv) ANTI-SENSE: NO (ix) FEATURE:
         (A) NAME/KEY: Modified-site
         (B) LOCATION:1
         (D) OTHER INFORMATION:/product= "OTHER"
             /note= "N-methyl Gly"

(xi) SEQUENCE DESCRIPTION: SEQ ID NO: 1:

Gly Lys Pro Arg
1

(2) INFORMATION FOR SEQ ID NO: 2:

(i) SEQUENCE CHARACTERISTICS:
         (A) LENGTH: 4 amino acids
         (B) TYPE: amino acid
         (C) STRANDEDNESS:
         (D) TOPOLOGY: linear (ii) MOLECULE TYPE: peptide
```

(iii) HYPOTHETICAL: NO (iv) ANTI-SENSE: NO (ix) FEATURE:
              (A) NAME/KEY: Modified-site
              (B) LOCATION:1
              (D) OTHER INFORMATION:/product= "OTHER"
                  /note= "D-Ala"

(xi) SEQUENCE DESCRIPTION: SEQ ID NO: 2:

Ala Lys Pro Arg
1

(2) INFORMATION FOR SEQ ID NO: 3:

(i) SEQUENCE CHARACTERISTICS:
            (A) LENGTH: 4 amino acids
            (B) TYPE: amino acid
            (C) STRANDEDNESS:
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 3:

Gly Pro Pro Arg
1

(2) INFORMATION FOR SEQ ID NO: 4:

(i) SEQUENCE CHARACTERISTICS:
            (A) LENGTH: 4 amino acids
            (B) TYPE: amino acid
            (C) STRANDEDNESS:
            (D) TOPOLOGY: linear (ii) MOLECULE TYPE: peptide (iii) HYPOTHETICAL: NO (iv) ANTI-SENSE: NO (ix) FEATURE:
            (A) NAME/KEY: Modified-site
            (B) LOCATION:1
            (D) OTHER INFORMATION:/product= "OTHER"
                /note= "Ac-Gly"

(xi) SEQUENCE DESCRIPTION: SEQ ID NO: 4:

Gly Lys Pro Arg
1

(2) INFORMATION FOR SEQ ID NO: 5:

(i) SEQUENCE CHARACTERISTICS:
            (A) LENGTH: 4 amino acids
            (B) TYPE: amino acid
            (C) STRANDEDNESS:
            (D) TOPOLOGY: linear (ii) MOLECULE TYPE: peptide (iii) HYPOTHETICAL: NO (iv) ANTI-SENSE: NO (ix) FEATURE:
            (A) NAME/KEY: Modified-site
            (B) LOCATION:2

(D) OTHER INFORMATION:/product= "OTHER"
                /note= "(Bzl)Lys"

(xi) SEQUENCE DESCRIPTION: SEQ ID NO: 5:

Gly Lys Pro Arg
1

(2) INFORMATION FOR SEQ ID NO: 6:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (iii) HYPOTHETICAL: NO (iv) ANTI-SENSE: NO (ix) FEATURE:
        (A) NAME/KEY: Modified-site
        (B) LOCATION:2
        (D) OTHER INFORMATION:/product= "OTHER"
            /note= "(isoBu)Lys"

(xi) SEQUENCE DESCRIPTION: SEQ ID NO: 6:

Gly Lys Pro Arg
1

(2) INFORMATION FOR SEQ ID NO: 7:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (iii) HYPOTHETICAL: NO (iv) ANTI-SENSE: NO (ix) FEATURE:
        (A) NAME/KEY: Modified-site
        (B) LOCATION:2
        (D) OTHER INFORMATION:/product= "OTHER"
            /note= "(Et)Lys"

(xi) SEQUENCE DESCRIPTION: SEQ ID NO: 7:

Leu Lys Pro Arg
1

(2) INFORMATION FOR SEQ ID NO: 8:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (iii) HYPOTHETICAL: NO (iv) ANTI-SENSE: NO (ix) FEATURE:
        (A) NAME/KEY: Modified-site
        (B) LOCATION:2
        (D) OTHER INFORMATION:/product= "OTHER"

/note= "(Et)Lys"

(xi) SEQUENCE DESCRIPTION: SEQ ID NO: 8:

Gly Lys Pro Leu
1

(2) INFORMATION FOR SEQ ID NO: 9:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 9:

Gly Lys Pro Arg
1

(2) INFORMATION FOR SEQ ID NO: 10:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (iii) HYPOTHETICAL: NO (iv) ANTI-SENSE: NO (ix) FEATURE:
        (A) NAME/KEY: Modified-site
        (B) LOCATION:2
        (D) OTHER INFORMATION:/product= "OTHER"
            /note= "D-Lys"

(xi) SEQUENCE DESCRIPTION: SEQ ID NO: 10:

Gly Lys Pro Arg
1

(2) INFORMATION FOR SEQ ID NO: 11:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (iii) HYPOTHETICAL: NO (iv) ANTI-SENSE: NO (ix) FEATURE:
        (A) NAME/KEY: Modified-site
        (B) LOCATION:2
        (D) OTHER INFORMATION:/product= "OTHER"
            /note= "(Et)Lys"

(xi) SEQUENCE DESCRIPTION: SEQ ID NO: 11:

Gly Lys Pro Arg